(12) United States Patent
Boles

(10) Patent No.: US 8,814,881 B2
(45) Date of Patent: Aug. 26, 2014

(54) DERMATOME WITH ORIENTATION GUIDES

(75) Inventor: David J. Boles, Copley, OH (US)

(73) Assignee: Zimmer Surgical, Inc., Dover, OH (US)

(*) Notice: Subject to any disclaimer, the term of this patent is extended or adjusted under 35 U.S.C. 154(b) by 481 days.

(21) Appl. No.: 11/955,732

(22) Filed: Dec. 13, 2007

(65) Prior Publication Data
US 2009/0157096 A1    Jun. 18, 2009

(51) Int. Cl.
*A61B 17/50* (2006.01)

(52) U.S. Cl.
USPC .......................................... 606/132; 606/167

(58) Field of Classification Search
USPC .......... 606/131, 132, 161, 166, 167, 171, 172; 30/34.2, 48, 51, 54, 55, 59, 75, 79, 30/478–493, 167, 167.1, 167.2, 282, 286, 30/289; 83/915.5
See application file for complete search history.

(56) References Cited

U.S. PATENT DOCUMENTS

| | | | |
|---|---|---|---|
| 1,935,605 A | 11/1933 | Atruda | |
| 2,288,709 A | 7/1942 | Hood | |
| 2,419,114 A * | 4/1947 | Briegel | 606/132 |
| 2,435,278 A | 2/1948 | Hood | |
| 2,457,772 A * | 12/1948 | Barron et al. | 606/132 |
| 2,691,377 A * | 10/1954 | Hood | 606/132 |
| 3,327,711 A | 6/1967 | Vallis | |
| 3,412,732 A * | 11/1968 | Simon | 606/132 |
| 3,428,045 A * | 2/1969 | Kratzsch et al. | 606/132 |
| 3,583,403 A | 6/1971 | Pohl et al. | |
| 3,670,734 A * | 6/1972 | Hardy, Jr. | 606/132 |
| 3,820,543 A * | 6/1974 | Vanjushin et al. | 606/132 |
| 3,857,178 A * | 12/1974 | Stevens, II | 30/344 |
| 3,890,704 A * | 6/1975 | Ferraro | 30/47 |
| 3,934,591 A | 1/1976 | Gleason | |
| 4,038,986 A | 8/1977 | Mahler | |
| 4,240,432 A | 12/1980 | Mormann et al. | |
| 4,270,540 A | 6/1981 | Schwartz | |
| 4,690,139 A | 9/1987 | Rosenberg | |
| 4,754,756 A | 7/1988 | Shelanski | |
| 4,838,284 A | 6/1989 | Shelanski | |
| 4,917,086 A * | 4/1990 | Feltovich et al. | 606/132 |
| 5,004,468 A | 4/1991 | Atkinson | |
| D322,672 S | 12/1991 | Feltovich et al. | |

(Continued)

FOREIGN PATENT DOCUMENTS

| | | |
|---|---|---|
| DE | 1566041 | 4/1970 |
| DE | 2234478 A1 | 4/1973 |

(Continued)

OTHER PUBLICATIONS

International Search Report from related PCT/US2008/086077; Feb. 17, 2009, 9 pages.

(Continued)

*Primary Examiner* — David Eastwood
(74) *Attorney, Agent, or Firm* — Seager, Tufte & Wickhem, LLC

(57) ABSTRACT

A dermatome has a blade that generally defines a plane and a body generally defining a longitudinal axis. The body also that has at least one flat outer surface for engaging the tissue and an end portion that is configured to hold the blade so that the plane of the blade is generally parallel to the longitudinal axis and non-parallel to the flat outer surface at a predetermined angle.

16 Claims, 3 Drawing Sheets

(56) References Cited

U.S. PATENT DOCUMENTS

| | | | |
|---|---|---|---|
| 5,208,984 A | 5/1993 | Negus | |
| 5,219,352 A | 6/1993 | Atkinson | |
| 5,342,379 A | 8/1994 | Volinsky | |
| 5,595,570 A | 1/1997 | Smith | |
| D401,340 S | 11/1998 | Waldman et al. | |
| 5,873,881 A | 2/1999 | McEwen et al. | |
| 5,921,980 A | 7/1999 | Kirn | |
| 6,080,166 A * | 6/2000 | McEwen et al. | 606/132 |
| 6,254,619 B1 * | 7/2001 | Garabet et al. | 606/166 |
| 6,422,780 B2 | 7/2002 | Chen | |
| 6,440,143 B2 | 8/2002 | Kasten | |
| 6,530,931 B1 | 3/2003 | Rosenberg | |
| 6,540,760 B2 | 4/2003 | Austring et al. | |
| 6,663,644 B1 | 12/2003 | Ross et al. | |
| 6,702,832 B2 * | 3/2004 | Ross et al. | 606/166 |
| 6,923,821 B2 | 8/2005 | Wortrich | |
| 6,993,818 B2 | 2/2006 | Smith et al. | |
| 7,166,117 B2 | 1/2007 | Hellenkamp | |
| 7,166,118 B2 | 1/2007 | Dame et al. | |
| 7,175,639 B2 | 2/2007 | Duprat et al. | |
| 7,208,000 B2 | 4/2007 | Love | |
| 2001/0000833 A1 | 5/2001 | Chen | |
| 2001/0047177 A1 | 11/2001 | Kasten | |
| 2003/0139755 A1 * | 7/2003 | Dybbs | 606/166 |
| 2004/0073246 A1 | 4/2004 | Aufaure et al. | |
| 2004/0172045 A1 | 9/2004 | Eriksson et al. | |
| 2004/0175690 A1 | 9/2004 | Mishra et al. | |
| 2004/0186498 A1 | 9/2004 | Barnes et al. | |
| 2004/0225309 A1 | 11/2004 | Eriksson et al. | |
| 2004/0230215 A1 | 11/2004 | Eriksson et al. | |
| 2004/0243150 A1 | 12/2004 | Werner | |
| 2005/0101972 A1 | 5/2005 | Bhatavadekar et al. | |
| 2005/0131435 A1 | 6/2005 | Halecki et al. | |
| 2005/0234485 A1 | 10/2005 | Seegert et al. | |
| 2006/0015124 A1 | 1/2006 | Floerke | |
| 2006/0271070 A1 | 11/2006 | Eriksson et al. | |
| 2007/0208362 A1 * | 9/2007 | Ross et al. | 606/166 |
| 2009/0138027 A1 * | 5/2009 | Lucas et al. | 606/132 |

FOREIGN PATENT DOCUMENTS

| | | | |
|---|---|---|---|
| DE | 1566041 B * | 2/1976 | |
| DE | 2916268 B1 | 4/1980 | |
| JP | 3016791 Y | 11/1955 | |
| JP | 3016792 Y | 11/1955 | |
| JP | 3016793 Y | 11/1955 | |
| JP | 3116943 U | 11/2005 | |
| JP | 2006517139 A | 7/2006 | |
| RU | 2086198 | 8/1997 | |
| RU | 2294167 | 9/2006 | |
| SU | 1184528 | 10/1985 | |
| WO | 2004071313 A2 | 8/2004 | |

OTHER PUBLICATIONS

Japanese Office Action dated Jul. 4, 2012 (3 pages).

* cited by examiner

DERMATOME WITH ORIENTATION GUIDES

FIELD OF THE INVENTION

The present invention relates to dermatomes for surgically harvesting grafts of skin for transplant, and particularly to dermatomes structured for a particular orientation relative to the tissue to be cut.

BACKGROUND

Conventional dermatomes are used for cutting skin tissue to obtain transplantable skin grafts. A skin graft is a patch of healthy skin that is harvested from one area of the body or donor site to cover a damaged or skinless area of the body. Typically, a dermatome has a front end holding a flat blade to be placed in contact with a tissue surface and a motor to oscillate the blade from side to side to create a slicing action which cuts the tissue as the dermatome is moved along the tissue surface.

In order to provide a smooth, continuous cut, a user attempts to hold the dermatome, and in turn the blade, steady at a defined angle relative to the tissue surface as the dermatome is moved over the skin. Typically, the known dermatome is held by tilting the dermatome by hand and at an angle of 30° to 45° relative to the tissue surface to provide a smooth, continuous cut. Oftentimes, this angle range is difficult to maintain do to the contouring of the tissue surface, or the practitioner simply does not carefully monitor the angle of the dermatome relative to the tissue surface. If a user fails to hold the dermatome steady and/or shifts the dermatome substantially away from a preferred angle range, an excessively deep cut or "skipping" may occur. When "skipping" occurs, the resulting graft will be inconsistent relative to thickness and may have areas where no skin has been harvested. Thus, a dermatome is desired that is easier to maintain at a specified angle range relative to the tissue surface it is cutting.

DETAILED DESCRIPTION

Figure 1:
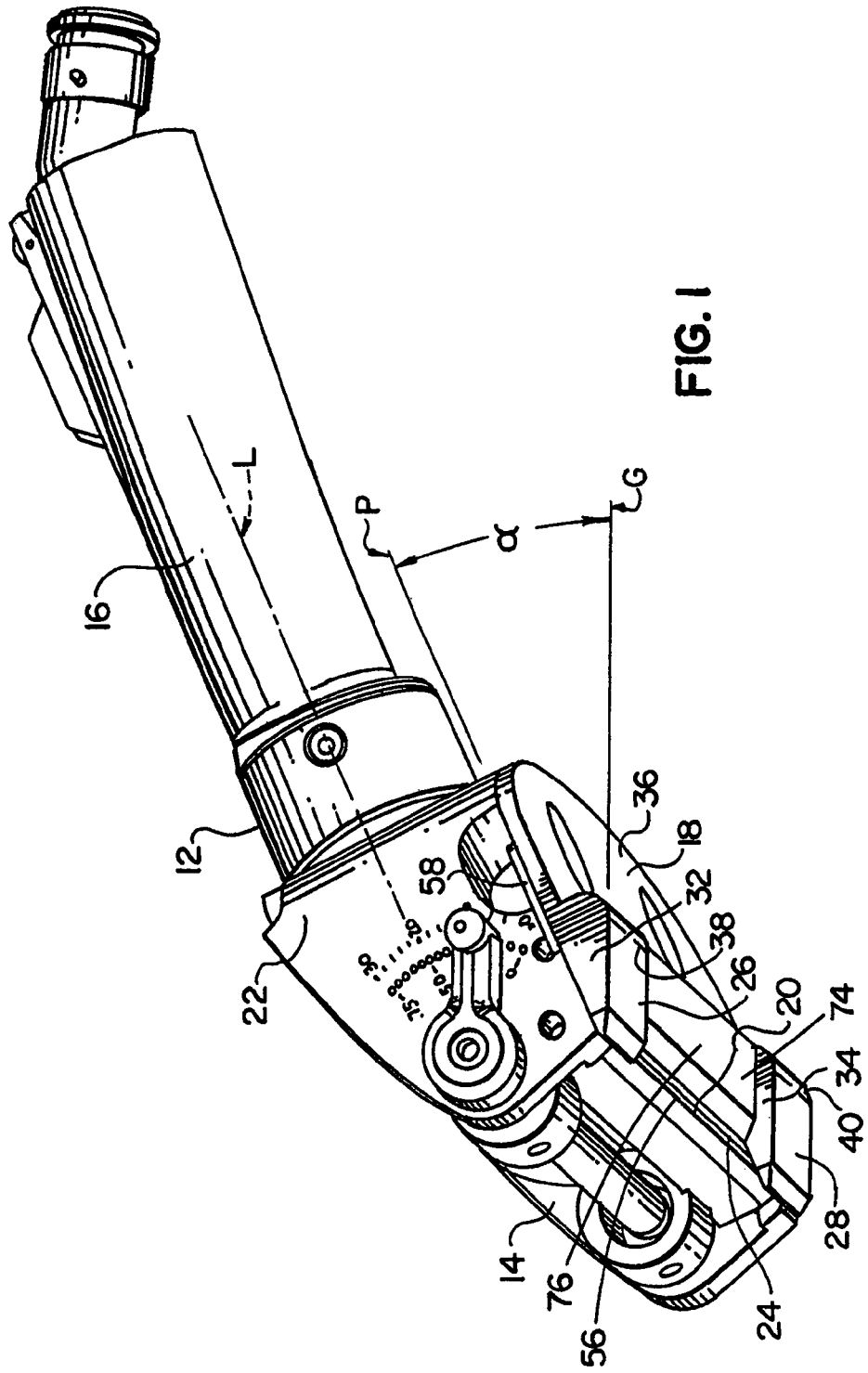
FIG. 1 is a left side perspective view of a dermatome according to one aspect of the present invention.
Figure 2:
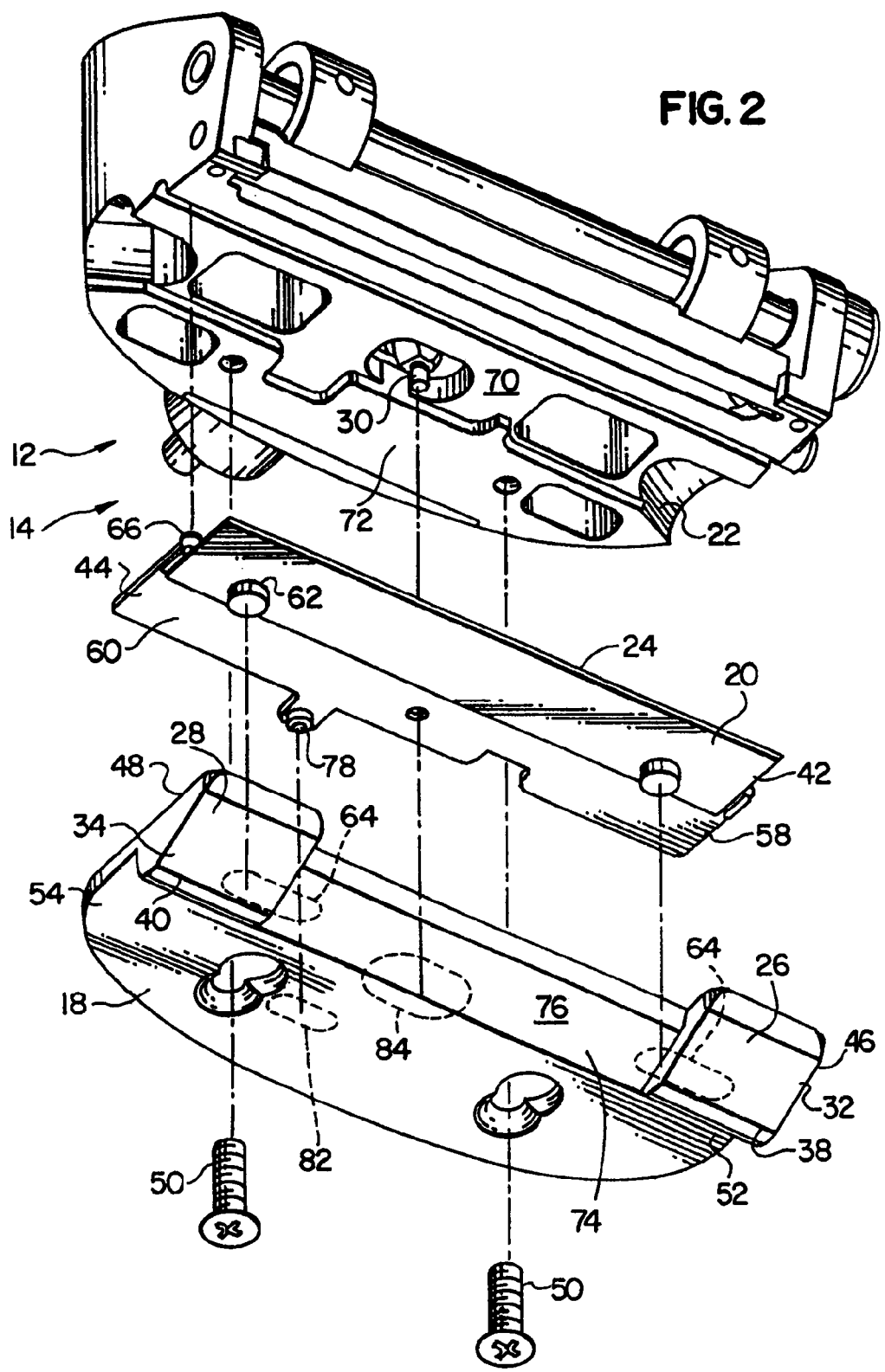
FIG. 2 is an exploded, lower perspective view of the dermatome of FIG. 1.
Figure 3:
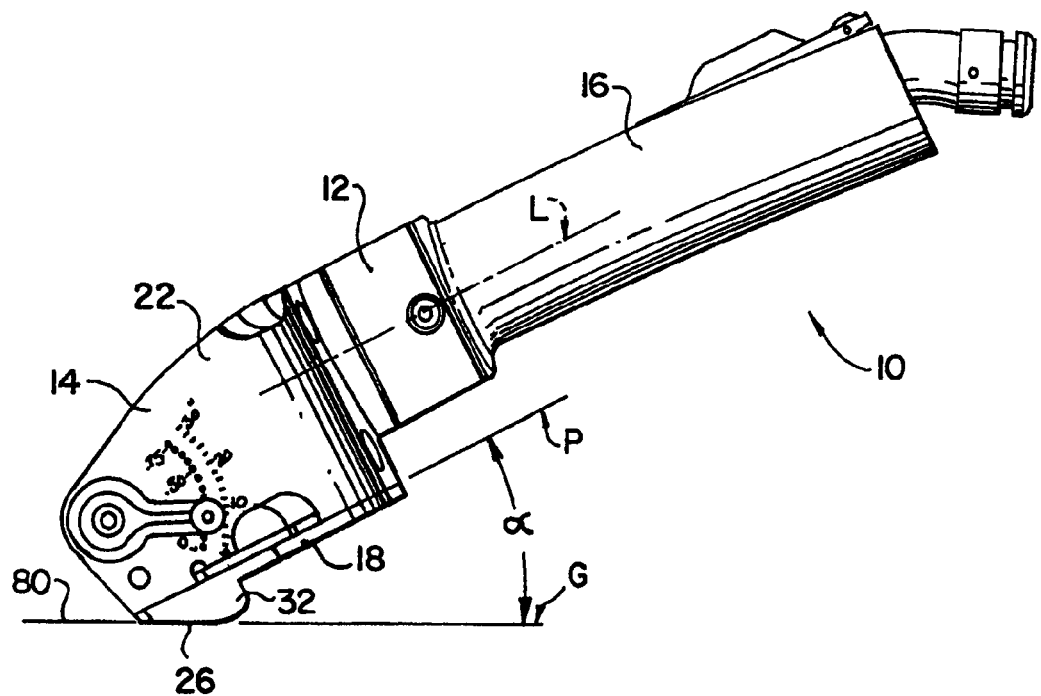
FIG. 3 is a left side elevational view of the dermatome of FIG. 1 shown placed against skin tissue to be cut.

Referring to FIGS. 1-3, a dermatome 10 has a body 12 with an end portion or head 14 connected to a handle 16. The head 14 has a bottom member (also referred to herein as a base member, bottom plate, or width plate) 18 that is detachable from a main head portion 22. A blade assembly 58 is mounted on the head 14 between the bottom member 18 and the main head portion 22. The blade assembly 58 has a flat blade 20 mounted on a carrier 60. The bottom member 18 is connected to the main head portion 22 by screws 50 or any other connection mechanism or adhesive as long as the bottom member 18 is able to secure the blade 20 and blade assembly 58 to the main head portion 22 while still permitting the blade 20 to oscillate transversely between the main head portion 22 and the bottom member 18 as explained in greater detail below. The blade 20 has a sharp blade edge 24 facing forward on the dermatome 10 and generally defines a plane P that is generally parallel to a longitudinal axis L. The axis L is generally defined by the dermatome 10 such that the handle 16 also generally extends along axis L. With this configuration, a user grasping the handle 16 can intuitively comprehend the orientation of the blade relative to the position of the handle 16, and in turn, the angle of the blade 20 relative to the tissue surface that the dermatome is placed against.

The body 12 has at least one lower, flat outer surface to maintain the blade at a predetermined angle relative to a tissue surface 80. In the illustrated form, the body 12 has left and right outer surfaces 26 and 28 that are configured to face and engage tissue surface 80. The outer surfaces 26 and 28 are sloped to extend upward toward the blade and plane P as outer surfaces 26 and 28 extend forward. The blade plane P extends non-parallel to the outer surfaces 26 and 28 at a predetermined angle α relative to a plane G cooperatively defined by the outer surfaces 26 and 28. In order to reduce skipping, excessively deep cuts and rough edges as well accelerated dulling of the blade edge 24, the predetermined angle α has a desired range of about 25° to 45°.

Also in the illustrated form, a third outer surface 76 on the body 12, and more specifically on the front of the bottom member 18, extends transversely between the outer surfaces 26 and 28. The outer surface 76 is flat and is set back from the outer surfaces 26 and 28. The outer surface 76 also extends generally parallel to the outer surfaces 26 and 28 to contact the tissue surface and add further stability to hold the blade 20 at the predetermined angle.

In operation, the sharp edge 24 of the blade 20 is placed against the tissue to be cut and the outer surfaces 26, 28 and 76 are placed flush against the tissue. This will orient the dermatome 10, and in turn the handle 16 as well as the blade 20, approximately at the predetermined angle α relative to the tissue surface 80 being cut as shown in FIG. 3. It will be understood that pressing the dermatome 10 against the tissue surface 80 will raise the tissue between the guides 32 and 34 to place the tissue in contact with the blade edge 24 as well as outer surface 76. The outer surface 76 is set back from outer surfaces 26 and 28 to provide the tissue clearance so that the tissue may be positioned in front of the sharp edge 24 of the blade 20.

The dermatome 10 has a motor with an oscillating drive pin 30 connected to the blade assembly 58 to transversely oscillate the blade 20 to create a side to side slicing action. The blade assembly 58 is able to oscillate because the bottom member 18 is placed flush against a lower surface 70 that is dropped from a lower head surface 72 of the main head portion 22. With the blade assembly disposed between the bottom member 18 and the head surface 72, the bottom member 18 restricts vertical movement of the blade assembly while the distance between the head surface 72 and the bottom member 18 provides sufficient clearance for the blade assembly 58 to oscillate transversely. The blade assembly 58, and in turn the blade 20, also is fixed by a number of pin and groove/slot connections that permit the blade to oscillate transversely along with pin 30 while fixing the blade longitudinally and rotationally. This includes downwardly extending pins 62 and 78 on the blade assembly 58 that fit in corresponding transversely extending slots 64 and 82 (shown in dashed line), respectively, on the bottom member 18. Upwardly extending pins 66 on the blade assembly 58 fit in an elongate transversely extending groove 68 on the main head portion 22. Also, a slot or recess 84 (shown in dashed line) located on the base member 18 is accessible from above to provide clearance for the drive pin 30.

To cut the tissue, dermatome 10 is advanced which slides the blade edge 24 forward against the tissue surface 80 to cut the tissue. During the cutting operation, the dermatome 10 and blade 20 can be easily maintained approximately at the predetermined angle α by maintaining the lower surfaces 26, 28 and 76 flush against the tissue. This provides a continuous cut that forms relatively clean, generally straight edges along the skin graft.

By one approach, the outer surfaces 26 and 28 are formed by at least one distinct guide. In the illustrated example, left and right guides 32 and 34 respectively form outer surfaces 26 and 28 and a middle guide or portion 74 extending transversely between the guides 32 and 34 form the middle outer surface 76. The guides 32, 34 and 74 extend outwardly from a main lower surface 36 of the body 12. The guides 32, 34 and 74 are generally wedge shaped and are tapered to extend upward as the guides extend forward to locate the outer surfaces 26, 28 and 76 (and plane G) at the desired angle relative to the plane P. With this configuration, the outer surfaces 26 and 28 further extend to and on distal free ends 38 and 40 of the guides 32 and 34 respectively.

The guides 32, 34 and 74 as well as lower surface 36, in one form, are formed by the detachable bottom member 18. It will be understood, however, that other lower portions of the body 12 may form the guides instead (such as on the head 14 rearward of the bottom plate 18, for example). Alternatively, the bottom of the head 14 may not be entirely covered by a detachable bottom member 18, and it can be understood that a bottom portion integral with the main head portion 22 could form the guides 32, 34 and/or 74 instead.

Each guide 32 and 34 may be respectively placed near one of the lateral sides 42 and 44 of the blade 20. In one configuration, each guide 32 and 34 is formed on a forwardly projecting extension 46 and 48 on the bottom member 18, and respectively on left and right lateral sides 52 and 54 of the bottom member 18. In this case, the lateral sides 42 and 44 of the blade 20 including the sharp edge 28 at the lateral sides are covered by the extensions 46 and 48. Accordingly, the blade 20 and sharp edge 28 remain uncovered by the bottom member 18 between the two guides 32 and 34 so that the blade 24 can engage tissue between the two guides 32 and 34. Thus, the uncovered part 56 of the sharp blade edge 24 defines the width of the skin graft that the blade 20 will cut.

With the illustrated configuration, the protruding guides 32 and 34 limit cutting of the tissue from an undesirable angle less than the predetermined angle α that could accelerate dulling of the blade 20 and could cause skipping, excessively deep cuts and rough edges. In other words, since the handle 16 extends on the opposite side of the guides 32 and 34 from the blade edge 24 in a longitudinal direction, and if the dermatome handle 16 is unintentionally shifted toward the tissue surface while the guides 32 and 34 remain in contact with the tissue surface, the guides 32 and 34 will act as a fulcrum. Thus, the movement of the dermatome handle 16 will cause the blade edge 24 to be lifted off of the tissue surface so that cutting at an angle less than the predetermined angle α is substantially avoided.

It will be appreciated that while guides 32, 34 and 74 are shown as a generally single continuous piece with a setback middle portion, other configurations are contemplated such as providing more than one separate guide. Alternatively, a single guide may be provided that generally extends across only one part of the width. Otherwise, multiple separate guides may or may not be uniformly spaced across the width of the body 12 or bottom member 18, to name a few examples.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

What is claimed is:

1. A dermatome comprising:
   a blade generally defining a plane;
   a body generally defining a longitudinal axis, the body including a head and a bottom plate having a first flat outer surface and a substantially coplanar second flat outer surface laterally spaced from the first flat outer surface for engaging tissue and extending at an acute angle relative to the longitudinal axis, the first flat outer surface and the second flat outer surface extending substantially horizontal as the body and longitudinal axis are held in an orientation for operating the dermatome, and the head having an end portion configured to hold the blade so that the plane generally extends parallel to the longitudinal axis and non-parallel to the first flat outer surface and the second flat outer surface at a predetermined angle relative to the first flat outer surface and the second flat outer surface, wherein the blade has a sharp cutting edge for engaging tissue and extending transversely to the longitudinal axis; and
   a third flat outer surface of the bottom plate extending continuously and substantially from the first flat outer surface to the second flat outer surface at a tissue facing side of the blade and along the cutting edge, the third flat outer surface being at least substantially parallel to and non-coplanar to the first flat outer surface and set back from the first flat outer surface and the second flat outer surface; and
   wherein the bottom plate is detachably attachable to the head and is detachable from the head while the plane of the blade held in the head extends parallel to the longitudinal axis.

2. The dermatome of claim 1, wherein the bottom plate further comprises a main portion, and at least one distinct guide extending outwardly from the main portion, and wherein the first flat outer surface and the second flat outer surface are formed by the at least one distinct guide for maintaining the blade at the predetermined angle.

3. The dermatome of claim 2, wherein the at least one distinct guide has a free distal end and wherein the first flat outer surface is formed on the free distal end.

4. The dermatome of claim 2, wherein the blade is further comprised of opposite first and second lateral sides; and
   the at least one distinct guide includes first and second guides extending outwardly from the main portion;
   wherein the first guide is positioned near the first lateral side of the blade and the second guide is positioned near the second lateral side of the blade.

5. The dermatome of claim 1, wherein the predetermined angle is approximately between 25 and 45 degrees.

6. The dermatome of claim 2 wherein the at least one distinct guide extends across substantially an entire width of the body.

7. The dermatome of claim 1 wherein the body further comprises a front end surface, and the first flat outer surface extends at least partially transverse to the front end surface.

8. The dermatome of claim 2 wherein the main portion comprises a generally flat base member extending underneath the blade, and wherein the at least one distinct guide extends at least partially transversely and outwardly away from the base member.

9. The dermatome of claim 2 wherein the at least one distinct guide is wedge shaped.

10. The dermatome of claim 2 wherein the cutting edge faces a forward direction, and the at least one distinct guide is generally wedge shaped and tapers toward the blade as it extends in the forward direction and has a rounded rearward end extending away from the forward direction.

11. The dermatome of claim 10 wherein the rounded rearward end of the at least one distinct guide is positioned within a perimeter of the bottom plate.

12. A dermatome for cutting a tissue surface comprising:
a blade generally defining a plane;
a body holding the blade, generally defining a longitudinal axis, and having a head with a bottom outer surface generally extending parallel to the longitudinal axis, and a bottom plate detachable from the bottom outer surface of the head having first and second guide members for engaging the tissue surface extending downwardly from, and transversely to, the bottom outer surface, the first and second guide members each having a flat outer surface[s] that are coplanar and are configured to maintain the blade at an orientation so that the plane generally extends non-parallel to the tissue surface and the blade is maintained at a predetermined angle relative to the tissue surface during cutting of the tissue surface, whereby the dermatome at the predetermined angle substantially provides a continuous cut without significant skipping; and
the bottom plate having a flat outer surface extending continuously between the first and second guide members at a tissue facing side of the blade and being at least substantially parallel to and non-coplanar to the flat outer surfaces of the first and second guide members, and being set back from the flat outer surfaces of the first and second guide members; and
wherein the bottom outer surface of the head is capable of being maintained in a parallel position relative to the longitudinal axis while the bottom plate is detached from the head.

13. The dermatome of claim 12, wherein the blade has a sharp edge, wherein the body has a handle extending on the opposite side of the first and second guide members and wherein the first and second guide members are configured to act as a fulcrum such that rotating the handle toward the tissue surface while the first and second guide members are in contact with the tissue surface removes the sharp edge from the tissue surface.

14. The dermatome of claim 12, wherein the predetermined angle is approximately between 25 and 45 degrees.

15. The dermatome of claim 12 wherein the first and second guide members are configured so that the blade is maintained at the predetermined angle while the dermatome is moved along the tissue surface.

16. The dermatome of claim 12 wherein the first and second guide members are wedge shaped.

* * * * *